(12) United States Patent
Kitao

(10) Patent No.: US 9,751,872 B2
(45) Date of Patent: Sep. 5, 2017

(54) COLORING COMPOUND AND TONER

(71) Applicant: CANON KABUSHIKI KAISHA, Tokyo (JP)

(72) Inventor: Akiko Kitao, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/197,554

(22) Filed: Jun. 29, 2016

(65) Prior Publication Data

US 2017/0001992 A1 Jan. 5, 2017

(30) Foreign Application Priority Data

Jul. 2, 2015 (JP) ................................. 2015-133453

(51) Int. Cl.
*G03G 9/09* (2006.01)
*C07D 417/06* (2006.01)
*C09B 23/04* (2006.01)

(52) U.S. Cl.
CPC ............ *C07D 417/06* (2013.01); *C09B 23/04* (2013.01); *G03G 9/0922* (2013.01)

(58) Field of Classification Search
CPC .. G03G 9/0924; G03G 9/0906; C07D 417/06; C09B 23/04
See application file for complete search history.

(56) References Cited

U.S. PATENT DOCUMENTS

| | | | |
|---|---|---|---|
| 5,545,235 A | 8/1996 | Sens | |
| 5,580,980 A | 12/1996 | Etzbach | |
| 5,654,122 A | 8/1997 | Etzbach | |
| 5,719,288 A | 2/1998 | Sens | |
| 5,785,719 A * | 7/1998 | Etzbach | C09B 23/04 8/471 |
| 6,528,223 B1 * | 3/2003 | Wilson | G03G 9/0906 430/108.21 |
| 8,940,087 B2 * | 1/2015 | Katsumoto | C07D 417/06 106/31.47 |
| 8,974,708 B2 * | 3/2015 | Shintou | C07D 417/06 252/586 |
| 2014/0080049 A1 * | 3/2014 | Ujifusa | G03G 9/0906 430/108.21 |
| 2014/0158955 A1 * | 6/2014 | Katsumoto | C07D 417/06 252/586 |
| 2014/0158956 A1 * | 6/2014 | Shintou | C07D 417/06 252/586 |
| 2014/0162183 A1 * | 6/2014 | Katsumoto | C09B 57/00 430/108.21 |
| 2014/0170552 A1 * | 6/2014 | Shintou | G03G 9/0906 430/108.21 |
| 2015/0232678 A1 * | 8/2015 | Okubo | C09D 11/326 347/20 |
| 2015/0378273 A1 * | 12/2015 | Mori | G03G 9/0806 430/108.23 |
| 2016/0303882 A1 * | 10/2016 | Shirota | B41M 5/3858 |

FOREIGN PATENT DOCUMENTS

| | | |
|---|---|---|
| DE | 4217973 A1 | 12/1993 |
| JP | 2003-195570 A | 7/2003 |
| JP | 2009-080478 A | 4/2009 |
| JP | 5-034980 A | 2/2013 |
| WO | 92/19684 A1 | 11/1992 |

OTHER PUBLICATIONS

John J. Ritter, A New Reaction of Nitriles. I. Amides from Alkenes and Monotriles, Contribution from the Chemical Laboratory of New York University, J. am. Chem, Soc., 70, 4045-4048, (1948).

* cited by examiner

*Primary Examiner* — Christopher Rodee
(74) *Attorney, Agent, or Firm* — Canon U.S.A., Inc. IP Division

(57) ABSTRACT

This invention aims at providing a compound capable of providing a toner having high covering power and a toner having high covering power, which is achieved by an azamethine acetyl amide-based compound having a specific structure.

4 Claims, No Drawings

COLORING COMPOUND AND TONER

BACKGROUND OF THE INVENTION

Field of the Invention

The present invention relates to a coloring compound and a toner.

Description of the Related Art

Under present circumstances, a color reproduction area in an image formed. by a color toner of each color of yellow, magenta, and cyan cannot completely cover a color reproduction area on a computer display screen. The technical barrier is caused by a difference in the principles that, while the computer display screen is visually recognized by an additive color process using transmitted light, an image formed by an electrophotography using color toners is visually recognized by a subtractive color process using reflected light. In recent years, in order to further improve the monitor color reproducibility, an example of using dyes with high color saturation and a high lightness value as coloring materials for color toners has been reported.

Japanese Patent Laid-Open. Nos. 2009-080478 and 5-034980 have report a toner containing a xanthene dye and German Patent Laid-Open No. 4,217,973, Specification and Japanese Patent Laid-Open No. 2003-195570 have report a toner containing a methine dye. In general, a dye-based colorant, has excellent transparency, and therefore a certain amount of coloring materials is required in order to increase covering power. However, the increase in the coloring material amount deteriorates the transparency and the color development properties intrinsic to dyes. Therefore, it has been required to develop dyes having high absorbance of chromophores per g.

SUMMARY OF THE INVENTION

The present invention provides a toner having high covering power.

The above-described purpose can be achieved by the use of the following compound.

More specifically, the present invention provides a compound having a structure represented by the following general formula (1).

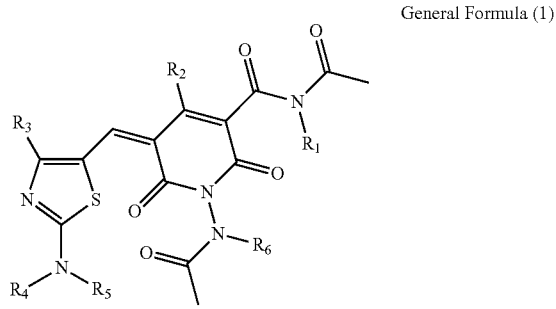

General Formula (1)

In General Formula (1), $R_1$ represents an alkyl group or an aralkyl group and $R_2$, $R_4$, and $R_5$ each independently represent an alkyl group. $R_3$ represents an alkyl group, a phenyl group not having a substituent, or a phenyl group having a substituent and the substituent in the phenyl group having the substituent is an alkyl group or an alkoxy group. $R_6$ represents an alkyl group or an acyl group.

The present invention provides a toner at least containing the compound. having the structure represented by General Formula (1) above.

Further features of the present invention will become apparent from the following description of exemplary embodiments.

DESCRIPTION OF THE EMBODIMENTS

Hereinafter, the present invention is described in more detail with reference to an embodiment.

The present inventors have conducted an extensive research in order to solve the above-described problems. a result, the present inventors have found that a toner having high covering power can be provided by blending a compound. having a structure represented by the following general formula (1) as a colorant. As factors which increase the covering power, it is considered that the compound has an acetyl group in each of a N—N ligand of a pyridone ring and a carboxylic amide group.

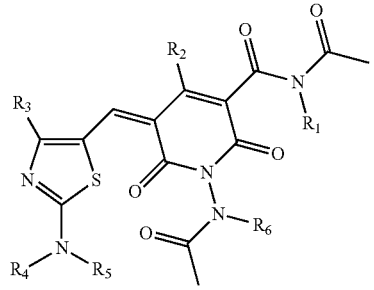

General Formula (1)

In General Formula (1), $R_1$ represents an alkyl group or an aralkyl group and $R_2$, $R_4$, and $R_5$ each independently represent an alkyl group. $R_3$ represents an alkyl group, a phenyl group not having a substituent, or a phenyl group having a substituent and the substituent in the phenyl group having the substituent is an alkyl group or an alkoxy group. $R_6$ represents an alkyl group or an acyl group.

First, the compound having the structure represented by General Formula (1) is described.

In General Formula (1), the alkyl group in $R_1$ is not particularly limited and saturated or unsaturated; linear, branched, or cyclic; and primary to tertiary; alkyl groups having 1 to 20 carbon atoms are mentioned. Examples of the alkyl groups include, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group.

In General Formula (1), the aralkyl group in $R_1$ is not particularly limited and a benzyl group, a trimethyl benzyl group, a dimethyl benzyl group, and the like are mentioned.

In General Formula (1), the alkyl group in $R_2$ is not particularly limited and saturated or unsaturated; linear or branched; and primary to tertiary; alkyl groups having 1 to 4 carbon atoms are mentioned. Examples of the alkyl groups include, for example, a methyl group, an ethyl group, an n-propyl group, an iso-propyl group, an n-butyl group, and a sec-butyl group.

In General Formula (1), the alkyl group in $R_3$ is not particularly limited and saturated or unsaturated; linear, branched, or cyclic; and primary to tertiary; alkyl groups having 1 to 20 carbon atoms are mentioned. Examples of the alkyl groups include, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group.

It is more suitable that $R_3$ has a structure represented by the following general formula (2).

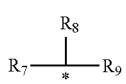

General Formula (2)

In General Formula (2), $R_7$ represents a hydrogen atom or an alkyl group, $R_8$ and $R_9$ each independently represent an alkyl group, and * represents a bonding site.

The alkyl groups in $R_7$ to $R_9$ are not particularly limited and alkyl groups having 1 to 4 carbon atoms, such as a methyl group, an ethyl group, an n-propyl group, an iso-propyl group, and an n-butyl group, are mentioned, for example. It is more suitable that $R_7$ to $R_9$ in General Formula (2) are all methyl groups (i.e., tert-butyl group). In this case, the compatibility with resin is improved and the color development properties are excellent.

In General Formula (1), the alkyl groups as the substituent of the phenyl group in $R_3$ are suitably alkyl groups having 1 to 4 carbon atoms, such as a methyl group, an ethyl group, an n-propyl group, an iso-propyl group, and an n-butyl group. Specific examples of a phenyl group substituted by an alkyl group include a dimethylphenyl group and a trimethylphenyl group. A 2,6-dimethyl phenyl group represented by the following formula (3) is more suitable.

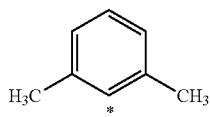

General Formula (3)

In Formula (3), * represents a bonding site.

In General Formula (1), examples of the alkoxy groups as the substituent of the phenyl group in $R_3$ include a methoxy group, an ethoxy group, a propoxyl group, a butoxy group, and a hexoxy group.

In General Formula (1), the alkyl groups in $R_4$ and $R_5$ are not particularly limited and saturated or unsaturated; linear, branched, or cyclic; and primary to tertiary; alkyl groups having 1 to 20 carbon atoms are mentioned. Examples of the alkyl groups include, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenyl group. In particular, a branched alkyl group, such as a 2-ethylhexyl group, is suitable because the compatibility with resin is improved and the color development properties are excellent.

In General Formula (1), the alkyl group in $R_6$ is not particularly limited and saturated or unsaturated; linear, branched, or cyclic; and primary to tertiary; alkyl groups having 1 to 20 carbon atoms are mentioned. Examples of the alkyl groups include, for example, a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group.

The acyl group in $R_6$ is not particularly limited and a formyl group, an acetyl group, a propionyl group, a benzoyl group, or a pivaloyl group is mentioned, for example.

The compound having the structure represented by General Formula (1) can be synthesized referring to a known method described in international Publication No. WO92/19684 and J. Am. Chem. Soc., 70, 4045 (1948). However, the manufacturing method is not always limited thereto.

The compound represented by General Formula (1) includes cis-trans structural isomers and both the cis type and the trans type belong to the technical scope of the present invention.

As suitable examples of the compound of the present invention, compounds (1) to (41) are shown below but the compound of the present invention is not particularly limited to the following compounds.

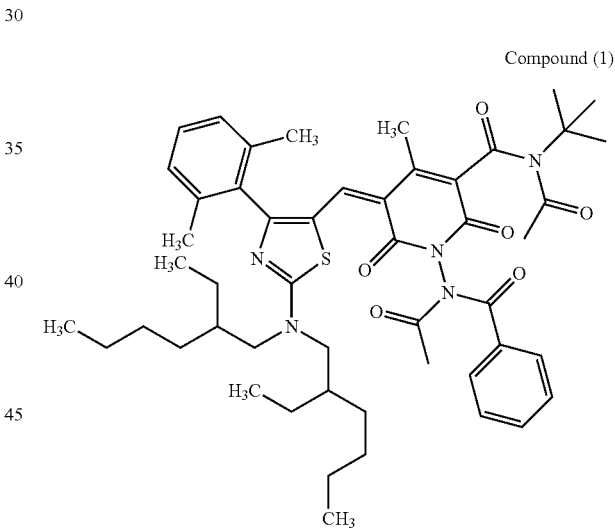

Compound (1)

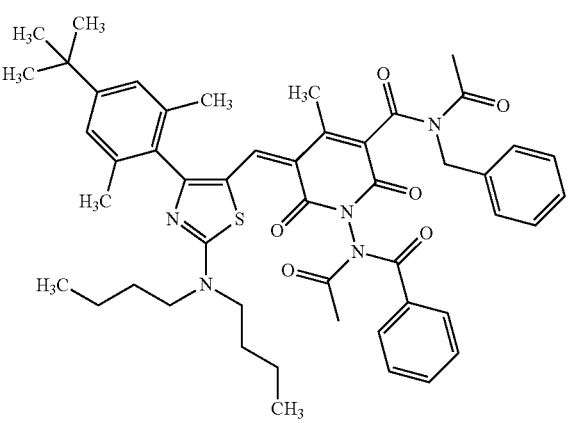

Compound (2)

Compound (3)
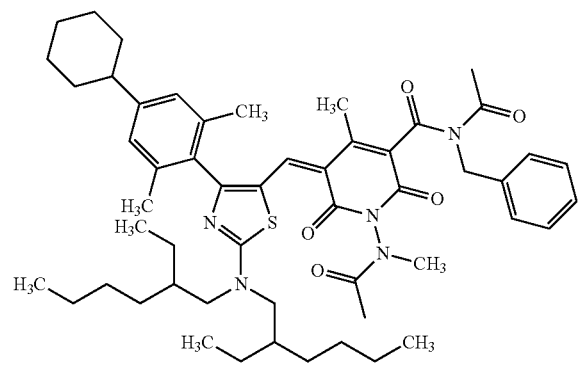
Compound (4)
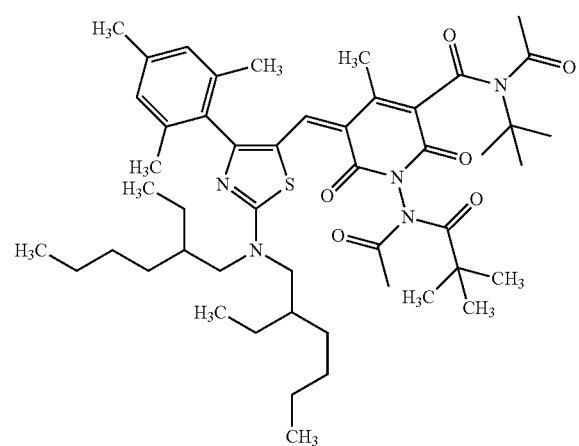
Compound (5)
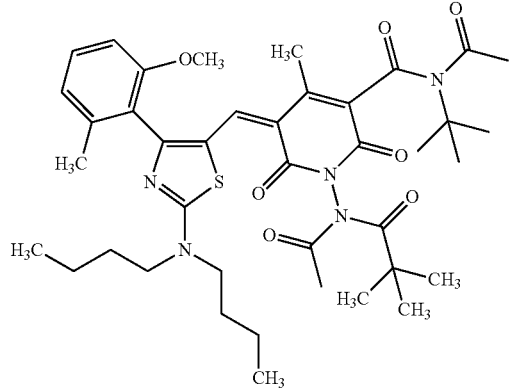
Compound (6)
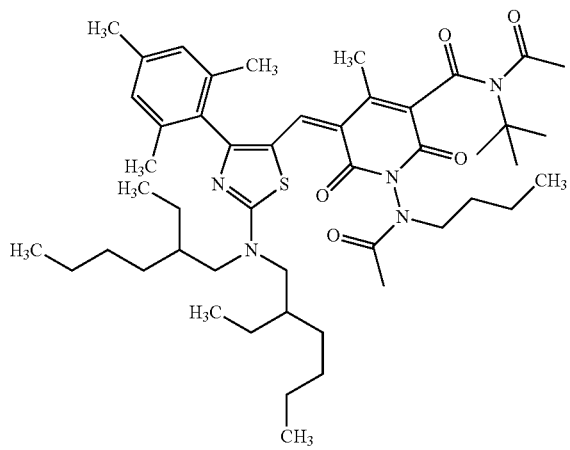
Compound (7)
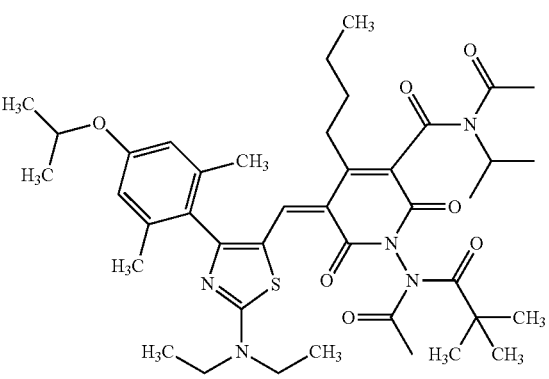
Compound (8)
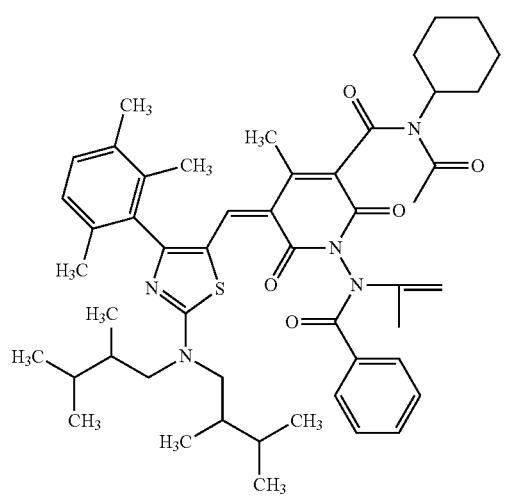

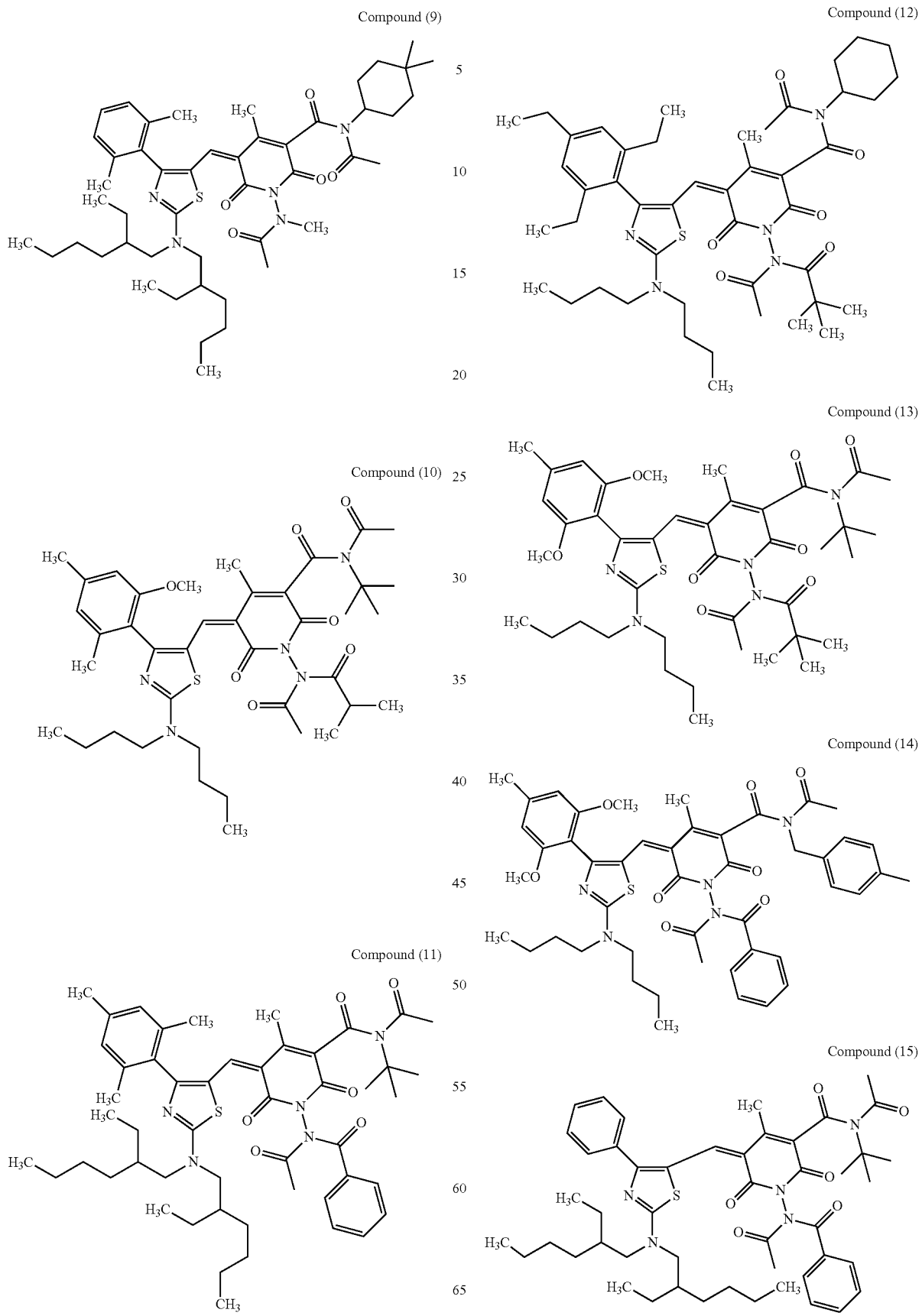

Compound (16)
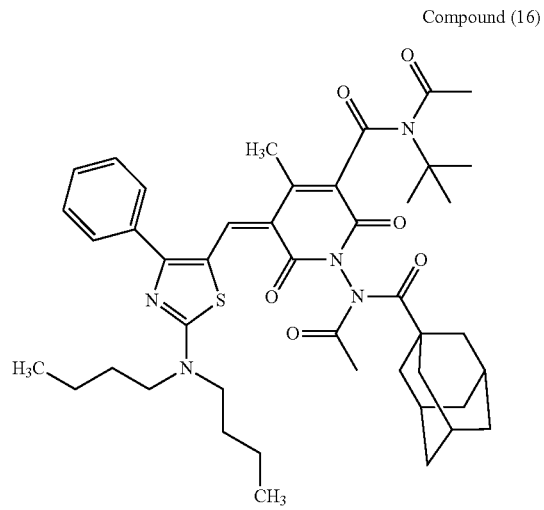
Compound (17)
Compound (18)
Compound (19)
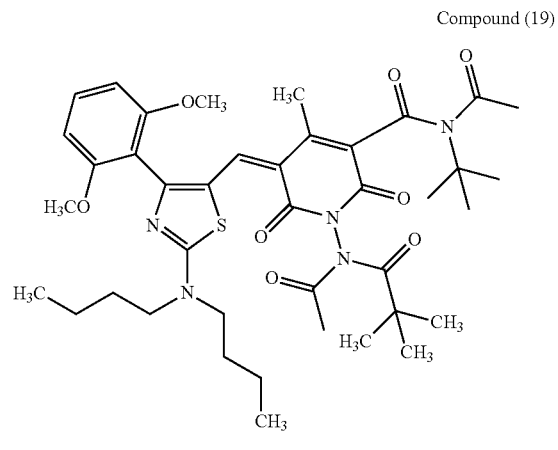
Compound (20)
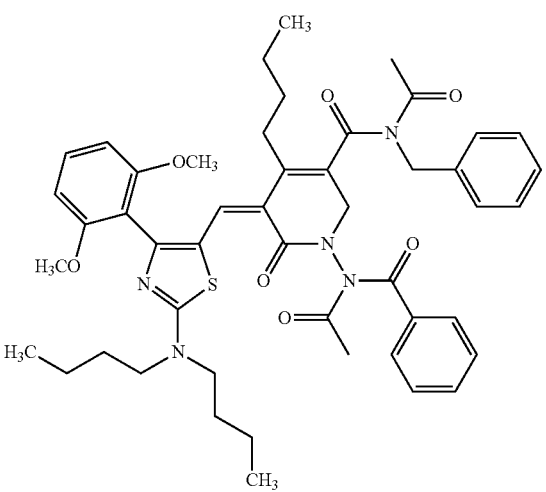
Compound (21)
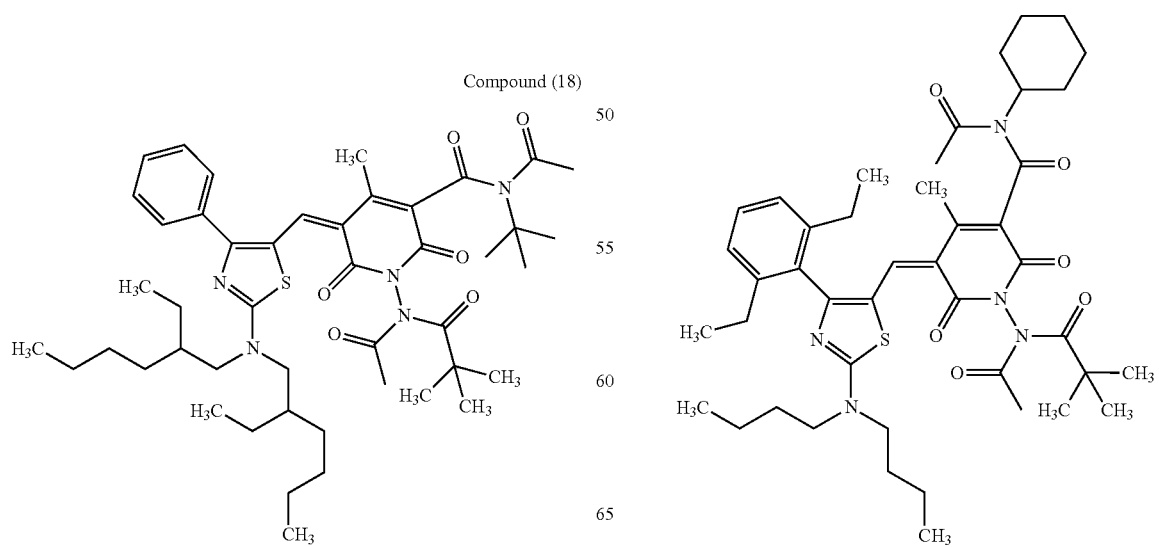

Compound (22)
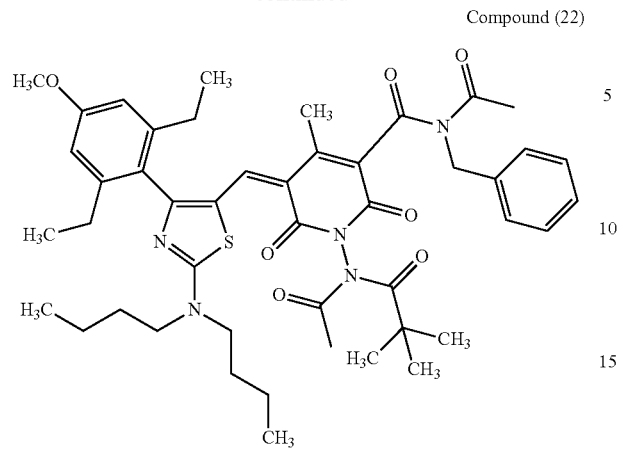
Compound (23)
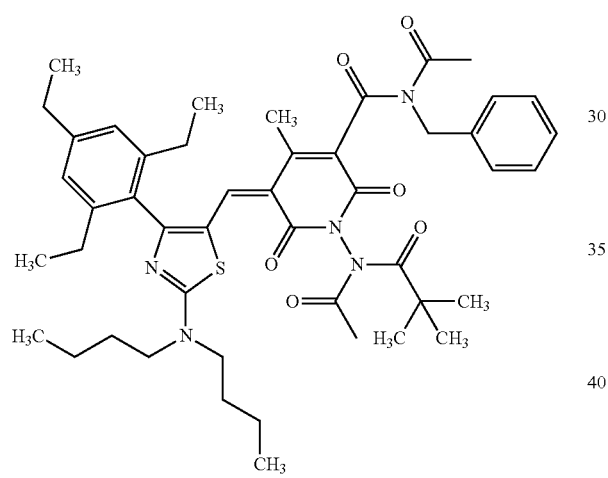
Compound (24)
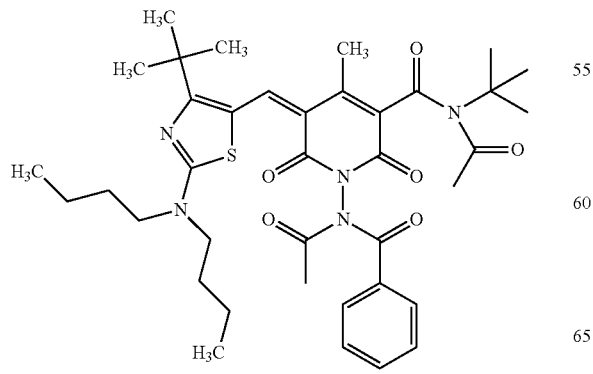
Compound (25)
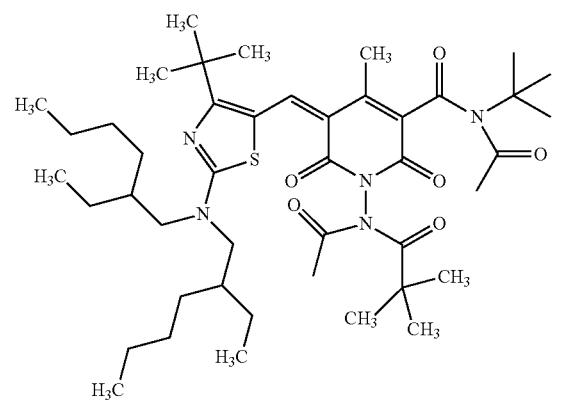
Compound (26)
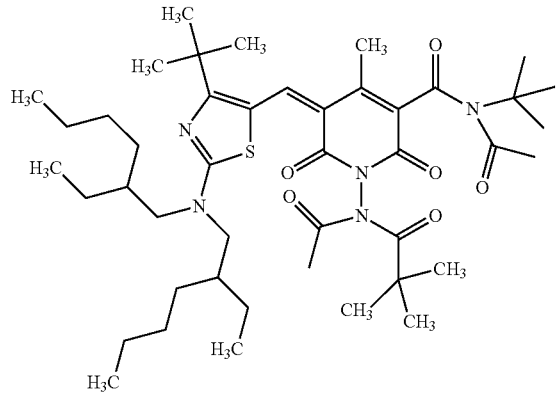
Compound (27)
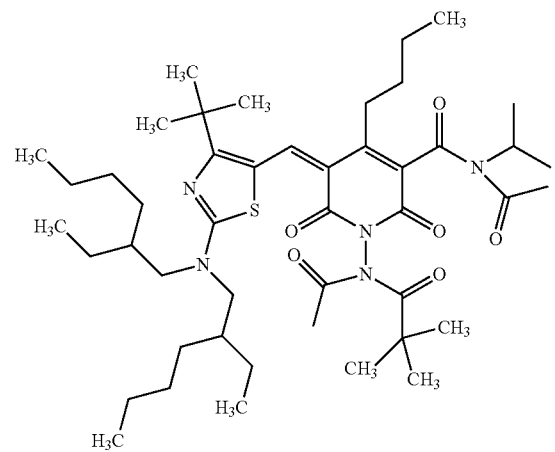

Compound (28)
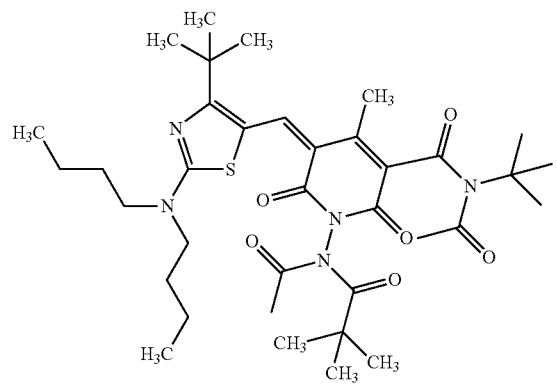
Compound (29)
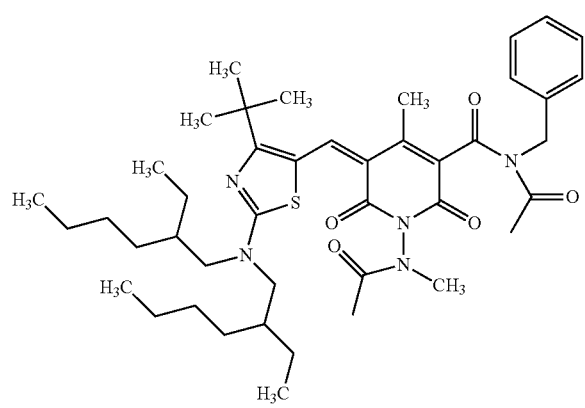
Compound (30)
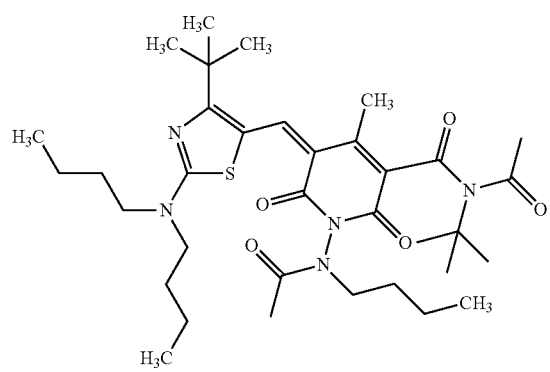
Compound (31)
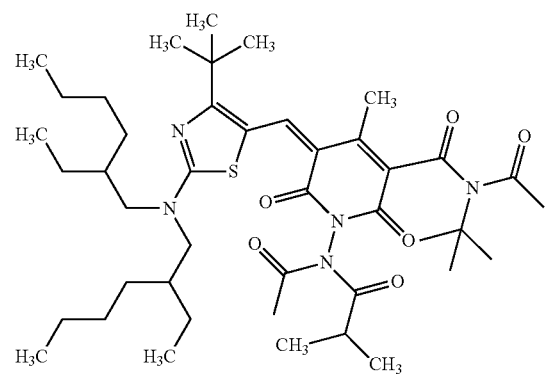
Compound (32)
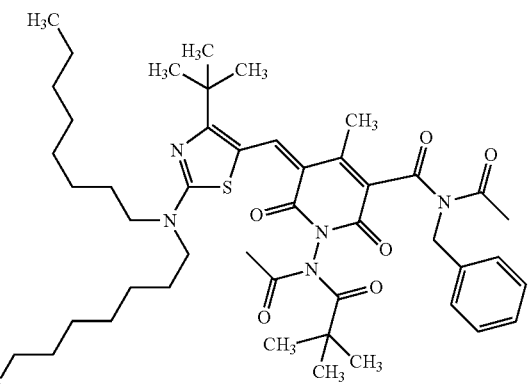
Compound (33)
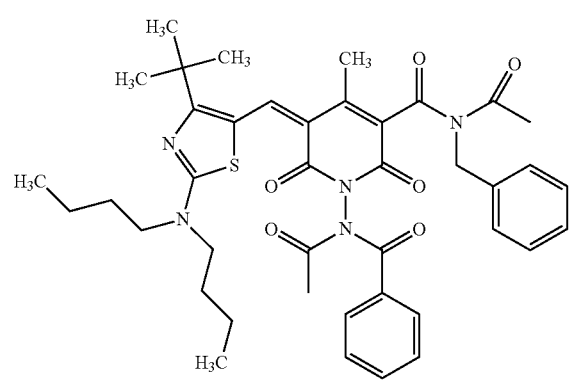
Compound (34)
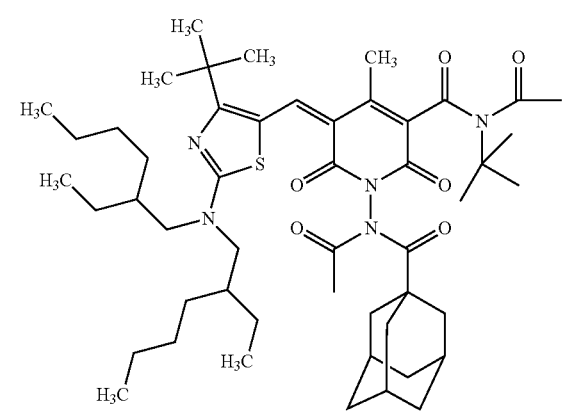
Compound (35)
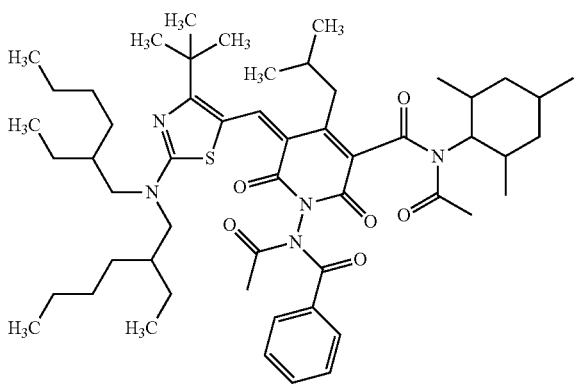

Compound (36)
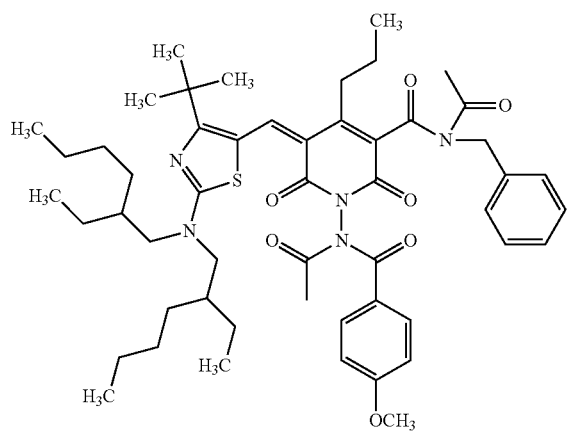

Compound (37)
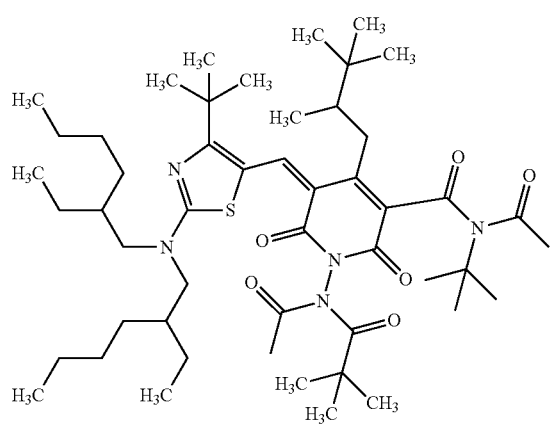

(Compound 38)
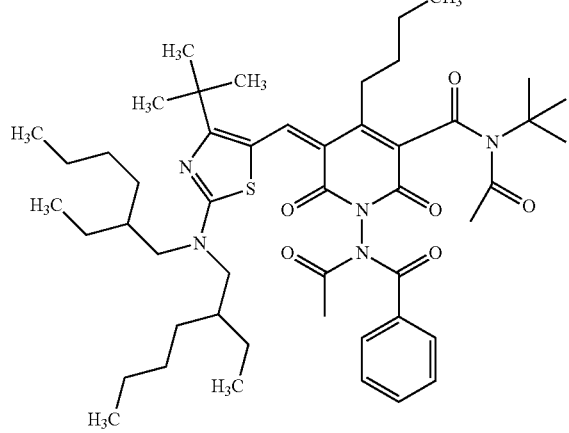

Compound (39)
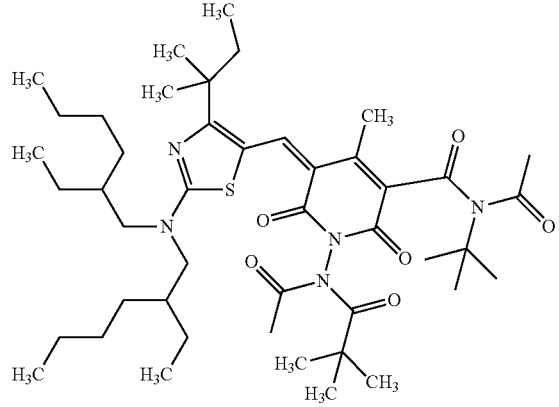

Compound (40)
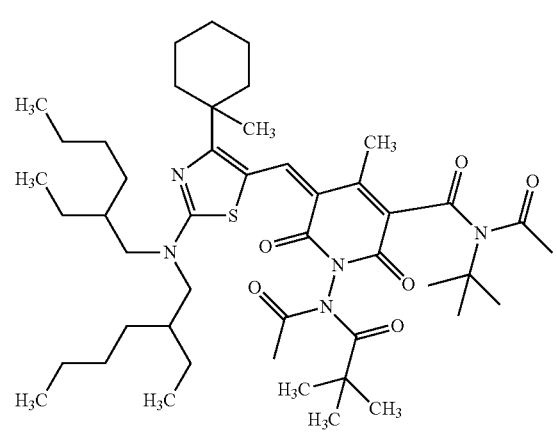

Compound (41)
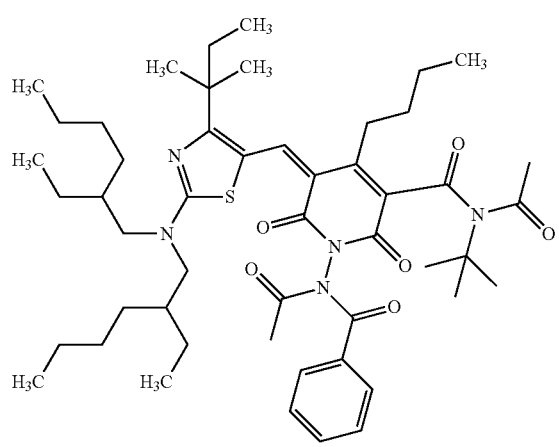

The compounds represented by General Formula (1) of the present invention may be used alone or in combination of two or more kinds thereof in order to adjust the color tone and the like. Furthermore, the compounds represented by General Formula (1) of the present invention can also be used in combination with known pigments and dyes.

Next, a toner of the present invention is described. First, constituent materials of the toner of the present invention are described.

About Binder Resin

A binder resin for use in the toner of the present invention is not particularly limited and, for example, a thermoplastic resin and the like can be mentioned.

Specifically, homopolymers or copolymers (styrene-based resin) of styrenes, such as styrene, p-chlorostyrene, and α-methylstyrene; homopolymers or copolymers (acrylic resin, styrene acrylic resin) of esters having vinyl groups, such as methyl acrylate, ethyl acrylate, n-propyl acrylate, n-butyl acrylate, lauryl acrylate, 2-ethylhexyl acrylate, methyl methacrylate, ethyl methacrylate, n-propyl methacrylate, lauryl methacrylate, and 2-ethylhexyl methacrylate, vinyl nitriles, such as acrylonitrile and methacrylonitrile, vinyl ethers, such as vinyl ethyl ether and vinyl isobutyl ether, vinyl methyl ketone, vinyl ethyl ketone, vinyl isopropenyl ketone, and the like;

homopolymers or copolymers (olefin-based resin) of olefins, such as ethylene, propylene, butadiene, and isoprene can be mentioned and, in addition thereto, non-vinyl condensation-type resin, such as epoxy resin, polyester resin, polyurethane resin, polyamide resin, cellulosic resin, and polyether resin, and graft polymers of the non-vinyl condensation-type resin and vinyl-based monomers are mentioned. The polyester resin is suitable. These kinds of resin may be used alone or in combination of two or more kinds thereof.

The polyester resin is a suitably used resin and is synthesized from acids and alcohols.

The acids are not particularly limited and, aliphatic dicarboxylic acid, dicarboxylic acid having a double bond, and dicarboxylic acid having a sulfonic acid group are mentioned. Specific examples of the acids include oxalic acid, maionic acid, succinic acid, glutaric acid, adipic acid, pimelic acid, suberic acid, azelaic acid, sebacic acid, 1,9-nonane dicarboxylic acid, 1,10-decane dicarboxylic acid, 1,11-undecane dicarboxylic acid, 1,12-dodecane dicarboxylic acid, 1,13-tridecane dicarboxylic acid, 1,14-tetradecane dicarboxylic acid, 1, 16-hexadecane dicarboxylic acid, 1,18-octadecane dicarboxylic acid, and lower alkyl esters and acid anhydrides thereof. In particular, the aliphatic dicarboxylic acid is suitable and it is more suitable that the aliphatic site in the aliphatic dicarboxylic acid is saturated hydrocarbon.

The alcohols are not particularly limited and aliphatic diols are suitable. Examples of the alcohols include, for example, ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-dodecanediol, 1,12-undecanediol, 1,13-tridecanediol, 1,14-tetradecanediol, 1,18-octadecanediol, and 1,20-eicosanediol.

When the number of terminal groups of the molecular chain of polyester-based resin increases, the environmental dependence in the charge characteristics of the toner becomes large. Therefore, the acid value is suitably 90 mgKOH/g or less and more suitably 50 mgKOH/g or less. The hydroxyl group value is suitably 50 mgKOH/g or less and more suitably 30 mgKOH/g or less.

In the present invention, a crosslinking agent can also be used in the synthesis of the binder resin in order to increase the mechanical strength of toner particles and also control the molecular weight of toner molecules.

Crosslinking agents to be used when styrene resin, acrylic resin, and styrene acrylic resin are used as the binder resin are not particularly limited and, for example, bifunctional crosslinking agents, such as divinylbenzene, bis(4-acryloxy-polyethoxyphenyl) propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, diacrylates of polyethylene glycols #200, #400, and #600, dipropylene glycol diacrylate, polypropylene glycol diacrylate, polyester type diacrylate, and those obtained by changing the diacrylate to dimethacrylate are mentioned.

Multifunctional crosslinking agents are not particularly limited and, for example, pentaerythritol triacrylate, trmethylolethane triacrylate, trimethylolpropane triacrylate, tetramethylolmethane tetracrylate, origoester acrylate and methacrylate thereof, 2,2-bis(4-methacryloxyphenyl)propane, diallyl phthalate, triallyl cyanurate, triallyl isocyanurate, and triallyl trimellitate are mentioned.

The content of the crosslinking agents suitably 0.05 to 10 parts by mass and more suitably 0.1 to 5 parts by mass based on 100 parts by mass of the monomers from the viewpoint of the fixability and the offset resistance of the toner.

About Wax

Wax means a material to be used for the purpose of preventing the offset in toner fixing.

The wax usable in the present invention is not particularly limited and, specifically, petroleum-based wax, such as paraffin wax, microcrystalline wax, and petrolatum, and derivatives thereof, montan wax and a derivative thereof, hydrocarbon wax obtained by a Fischer-Tropsch process and a derivative thereof, polyolefin wax typified by polyethylene and a derivative thereof, and natural wax, such as carnauba wax and candelilla wax and derivatives thereof are mentioned. The derivatives also include oxides, block copolymers with vinyl monomers, and graft-modified products. Moreover, alcohols, such as higher aliphatic alcohols, aliphatic series, such as stearic acid, and pulmitic acid or compounds thereof, acid amide, ester, ketone, hydrogenated castor oil and a derivative thereof, vegetable wax, and animal wax are mentioned. These substances can be used alone or in combination.

As the addition amount of the wax component, the content of the wax component based on 100 parts by mass of the binder resin. is suitably in the range of 2.5 to 15 parts by mass and more suitably in the range of 3.0 to 10 parts by mass in total. When the addition amount of the wax component is 2.5 parts by mass or more, oilless fixing does not become difficult to achieve. When the addition amount thereof is 15 parts by mass or less, the amount of the wax component in the toner particles is not excessively large, and therefore the deterioration of desired charge characteristics due to the presence of excess wax components on the toner particle surface does not occur.

About Colorant

As the colorant in the toner of the present invention, the compounds represented by General Formula (1) may be used alone or as a mixture of two or more kinds thereof. Moreover, other colorants can be also used in combination as necessary.

Examples of the other colorants which can be used in combination include, but are not particularly limited thereto, condensed azo compounds, azo metal complexes, diketopyrrolopyrrole compounds, anthraquinone compounds, quinacridone compounds, basic dye lake compounds, naphthol compounds, benzimidazolone compounds, thioindigo compounds, perylene compounds, methine compounds, and allyl amide compounds. Specific examples of the other colorants include C.I. Pigment Orange 1, 5, 13, 15, 16, 34, 36, 38, 62, 64, 67, 72, and 74; C.I. Pigment Red 2, 3, 4, 5, 6, 7, 12, 16, 17, 23, 31, 32, 41, 48, 48:1, 48:2, 48:3, 48:4, 53:1, 57:1, 81:1, 112, 122, 123, 130, 144, 146, 149, 150, 166, 168, 169, 170, 176, 177, 178, 179, 181,184, 180, 187, 190, 194, 202, 206, 208, 209, 210, 220, 221, 224, 238, 242, 245, 253, 254, 255, 258, 266, 269, and 282; C.I. Pigment Violet :3, 19, 25, 32, and 50, and various compounds classified as derivatives thereof.

The content of these colorants is suitably 1 to 20 parts by mass in total based on 100 parts by mass of the binder resin in the toner.

About Charge Control Agent

In the toner of the present invention, a charge control agent can be mixed as necessary for use. This makes it possible to optimally control the triboelectric charging amount according to a development system.

As the charge control agent, known substances can be utilized and charge control agents which have high charge speed and can stably maintain a fixed charge amount are particularly suitable. When the toner is manufactured by a direct polymerization method, charge control agents which have low polymerization inhibition properties and are substantially free from soluble substances in an aqueous dispersion medium are particularly suitable.

Examples of the charge control agents include, for example, those which negatively charge the toner, such as polymers or copolymers having a sulfonic acid group, a sulfonic acid salt group, or a sulfonic ester group, salicylic acid derivatives and metal complexes thereof, monoazo metallic compounds, acetyl acetone metallic compounds, aromatic oxycarboxylic acids, aromatic mono- and polycarboxylic acids, metal salts, anhydrides, and esters thereof, phenol derivatives, such as bisphenol, urea derivatives, matal containing naphthols acid-based compounds, boron compounds, quarternary ammonium salts, calixarene, and resin-based charge control agents.

Examples of charge control agents which positively charge the toner include, for example, nigrosine-modified substances by nigrosine, fatty acid metal salts, and the like, guanidine compounds, imidazole compounds, quarternary ammonium salts, such as tributyl benzyl ammonium-1-hydroxy-4-naphthosulfonic acid salt and tetrabutyl ammonium tetrafluoroborate, onium salts, such as phosphonium salts which are analogues thereof, lake pigments thereof, triphenylmethane dyes and lake pigments thereof (Examples of laking agents include phosphotungstic acid, phosphomolybdic acid, phosphotungstic molybdic acid, tannic acid, lauric acid, gallic acid, ferricyanide, ferrocyanide, and the like.), metal salts of higher fatty acids, diorganotin oxides, such as dibutyltin oxide, dioctyltin oxide, and dicyclohexyltin oxide, diorganotin borates, such as dibutyltin borate, dioctyltin borate, and dicyclohexyltin borate, and resin-based charge control agents. These charge control agents may be used alone or in combination of two or more kinds thereof.

About Fluidizer

In the toner of the present invention, inorganic fine powder may be externally applied as a fluidizer. As the inorganic fine powder, fine powder of silica, titanium oxide, alumina, composite oxides thereof, those obtained by performing surface treatment thereto, and the like can be used.

Physical Properties of Toner

It is suitable for the toner of the present invention to have a weight average particle diameter D4 of 4.0 to 9.0 μm and have a ratio of the weight average particle diameter D4 to the number average particle diameter D1 (hereinafter referred to as D4/D1) of less than 1.35. It is more suitable that the weight average particle diameter D4 is 4.9 to 7.5 μm and the D4/D1 is less than 1.30. In the case where the proportion of fine powder having a value of the weight average particle diameter D4 of less than 4.0 μm increases, charge stabilization is difficult to achieve when the toner is applied to an electrophotographic development system, and thus image degradation, such as image fogging and development stripes, are likely to occur in continuous development operation (endurance operation) of a large number of sheets. In particular, when the proportion of fine powder of 2.5 μm or less increases, the tendency becomes more remarkable. When the proportion of fine powder having the weight average particle diameter D4 of more than 8.0 μm increases, the reproducibility of a half-tone part sharply decreases, so that images to be obtained are rough image, which are not suitable. In particular, when the proportion of coarse powder of 10.0 μm or more increases, the tendency more notably appears. When the D4/D1 exceeds 1.35, fogging and a decrease of transferability occur and also the thickness of the line width of thin lines and the like considerably varies, so that sharpness decreases.

A method for adjusting the weight average particle diameter D4 and the number average particle diameter D1 of the toner of the present invention varies depending on methods for manufacturing toner base particles. For example, in the case of a suspension polymerization method, the weight average particle diameter D4 and the number average particle diameter D1 can be adjusted by controlling the concentration of a dispersant, the reaction stirring speed or the reaction stirring time, and the like to be used in the preparation of an aqueous dispersion medium.

The average circularity measured with a flow type particle image analyzer of the toner of the present invention is 0.930 to 0.995 and more suitably 0.960 to 0.990 from the viewpoint of the transferability of the toner.

Method for Manufacturing Toner

Examples of methods for manufacturing the toner of the present invention include a pulverization method, a suspension polymerization method, a suspension granulation method, an emulsion polymerization method, an emulsion aggregation method, and the like which have been used heretofore. From the viewpoint that the environmental load in manufacturing is low and the controllability of the particle diameter is excellent, it is suitable to manufacture the toner by manufacturing methods including performing granulation in an aqueous medium, such as a suspension polymerization method and a suspension granulation method.

Liquid Developing Agent

The toner of the present invention can also be used for a developing agent to be used in a liquid development method (hereinafter referred to as a liquid developing agent).

Hereinafter, a method for manufacturing the liquid developing agent is described.

First, the liquid developing agent is manufactured by dissolving or dispersing the compound represented by General Formula (1), resin, and, as necessary, assistants, such as a charge control agent and wax, in an electrical insulation carrier liquid. Alternatively, the liquid developing agent may be prepared by a two-step method including first preparing a concentrated toner, and then diluting the concentrated toner with an electrical insulation carrier liquid to prepare a developing agent. To the compound represented by General Formula (1) of the present invention, coloring compounds, such as known pigments and dyes, may be added alone or in combination of two or more kinds thereof.

Usable dispersion machines are not particularly limited and, for example, media type dispersion machines, such as a rotation shearing type homogenizer, a ball mill, a sand mill, and an attritor, a high-pressure counter collision type dispersion machine, and the like are suitably used, for example.

Usable wax and resin are the same as those mentioned above.

The charge control agent is not particularly limited insofar as it is generally used in the liquid developing agent. Examples of the charge control agent include, for example, cobalt naphthenate, copper naphthenate, copper oleate, cobalt oleate, zirconium octylate, cobalt octylate, sodium dodecylbenzenesulfonate, calcium dodecylbenzenesulfonate, soy lecithin, and aluminum octoate.

The electrical insulation carrier liquid is not particularly limited and organic solvents having high electrical resistance of $10^9 \Omega \cdot cm$ or more and a low dielectric constant of 3 or less are suitably used, for example. As specific examples, substances having a boiling point in a temperature range of 68 to 250° C., such as aliphatic hydrocarbon solvents, e.g., hexane, pentane, octane, nonane, decane, undecane, and dodecane, Isopar H, G, K, L, and M (manufactured by Exon Chemistry), Linealene Dimer A-20 and A-20H (manufactured by Idemitsu Kosan), are suitable. These substances may be used alone or in combination of two or more kinds thereof in a range where the viscosity of the system does not become high.

EXAMPLES

Hereinafter, the present invention is described in more detail with reference to Examples and Comparative Examples but the present invention is not particularly limited, to the Examples. In the description, "part(s)" and "%" are based on mass unless otherwise particularly specified.

The identification of the obtained reaction products was performed by a plurality of analysis methods using devices mentioned. below. More specifically, as the used analyzers, $^1$H nuclear magnetic resonance spectroscopic analysis (ECA-400, manufactured by JEOL Co., Ltd.) and MALDI MS (autoflex device, manufactured by Bruker Daltonics K.K.) were used. In the MALDI MS, a negative mode was adopted for detection ions.

Synthesis Example 1: Manufacturing of Compound (1)

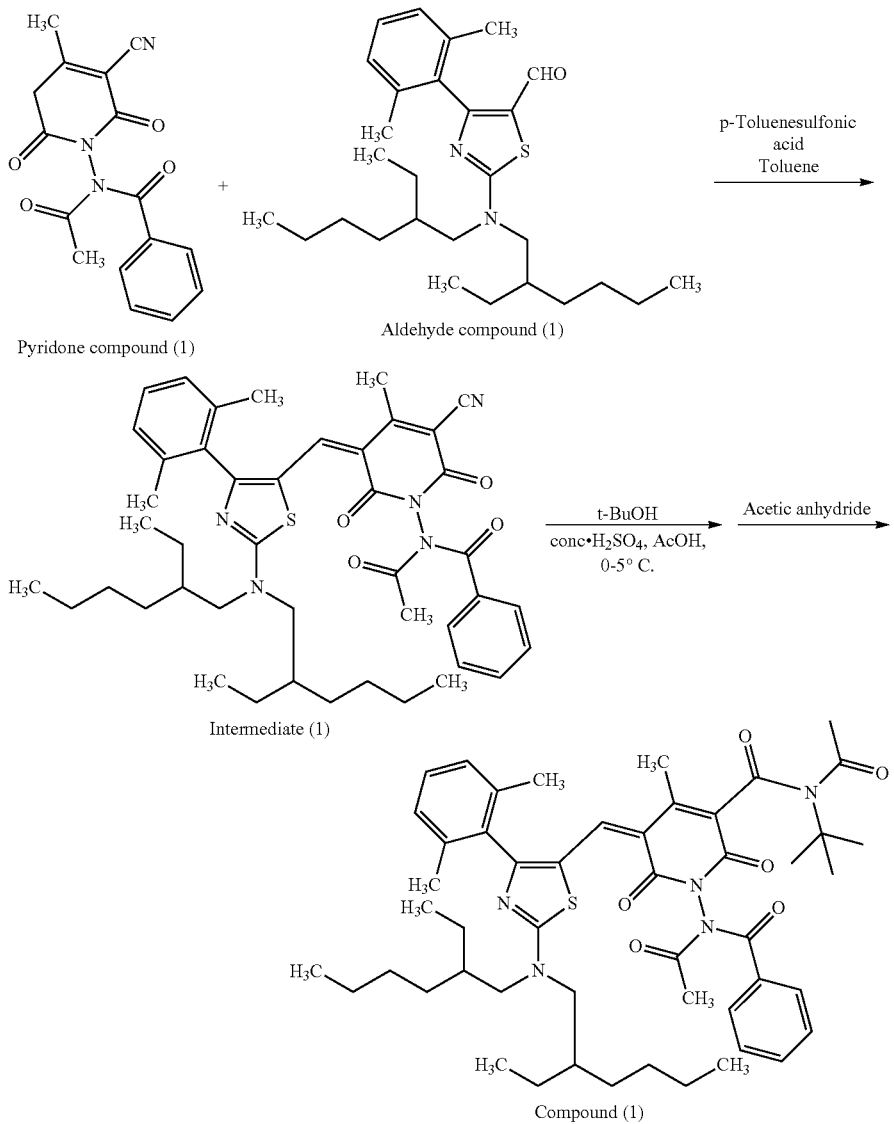

100 mg of p-toluenesulfonic acid was added to a suspension of 10 mmol of a pyridone compound (1) in 20 ml toluene, the temperature was increased to 70° C., and then a solution of 10 mmol of an aldehyde compound (1) in 20 mL of toluene was added dropwise to the mixture. Furthermore, the resultant mixture was refluxed under heating at 160° C. for 6 hours while performing azeotropic dehydration. After the completion of the reaction, the resultant mixture was cooled to room temperature, and then diluted with isopropanol. After concentrated under reduced pressure, the residue was purified by column chromatography (Developing solvent: Ethylacetate/Heptane).

5 mL of concentrated sulfuric acid and 15 mL of acetic acid were added, and then the mixture is stirred under ice cooling. 15 mmol of intermediate (1) is gradually added. while holding the temperature at 0 to 5° C. Furthermore, 35 mmol of t-butanol is added dropwise at the same temperature. After the dropwise addition, the resultant mixture is stirred for 1 hour while holding the solution at 0 to 5° C., and then the liquid temperature is gradually returned to room temperature.

After the completion of the reaction, the reaction liquid was poured into 500 mL of water. The deposited precipitate is filtered, extracted with chloroform, and then washed with a sodium hydrogencarbonate solution. The organic layer was dried over sodium sulfate, and then concentrated under reduced pressure. Thereafter, 30 ml of acetic anhydride was added to the residue, and then the mixture was stirred at 150° C. for 3 hours under an argon atmosphere. The reaction solution was allowed to cool, 50 mL of methanol was added, the mixture was stirred at room temperature for 1 hour, and then the resultant mixture was condensed under reduced pressure. The obtained residue was purified by column chromatography (Developing solvent: Ethylacetate/Heptane). 4.8 g of a compound (1) was obtained.

Analysis Results on Compound (1)
[1] Mass spectrometry by MALDI-TOF-MS: m/z=864.383 (M)

Synthesis Examples 2 to 4: Manufacturing of Compounds (15), (17), and (24)

Compounds (15), (17), and (24) were obtained by the same operation as that of Synthesis Example 1, except changing the pyridone compound (1) and the aldehyde compound (1) to the corresponding pyridone compounds and aldehyde compounds, respectively, in the Synthesis Example 1.

It was identified by the above-described analysis that the compounds were target substances.

Analysis Result on Compound (15)
[1] Mass spectrometry by MALDI-TOF-MS: m/z=837.457 (M)

Analysis Result on Compound (17)
[1] Mass spectrometry by MALDI-TOF-MS: m/z=837.329 (M)

Analysis Result on Compound (24)
[1] Mass spectrometry by MALDI-TOF-MS: m/z=704.561 (M)

Manufacturing of Toner

Toners of the present invention and toners for comparison were manufactured by the method described below.

Example 1: Manufacturing of Toner (1)

A mixture of 6 parts of the compound (1) which is the compound of the present invention and 120 parts of styrene were dispersed for 3 hours by an attritor (manufactured by NIPPON COKE &. ENGINEERING CO., LTD.) to obtain a colorant dispersion (1).

In a 2 L four-necked flask having a high-speed stirring device T.K. homomixer (manufactured by PRIMIX Corporation), 710 parts of ion exchange water and 450 parts of a 0.1 mol/L-trisodium phosphate aqueous solution were added, the number of rotations was adjusted to 12000 rpm, and the mixture was warmed. to 60° C. 68 parts of 1.0 mol/L-calcium chloride aqueous solution was gradually added thereto to prepare an aqueous dispersion medium containing micro-poorly water soluble dispersion stabilizer calcium phosphate.

Colorant dispersion (1) 133.2 parts
Styrene monomer 46.0 parts
n-butyl acrylate monomer 34.0 parts
Aluminum salicylate compound 2.0 parts
(BONTRON E-88, manufactured by Orient Chemical Industries Co., Ltd.)
Polyester resin 10.0 parts
(Polycondensation of propylene oxide-modified bisphenol A and isophthalic acid, Glass transition temperature Tg=65° C., Weight average molecular weight Mw=10000, Number average molecular weight Mn=6000)
Ester wax 25.0 parts
(Peak temperature of the maximum endothermic peak in DSC measurement=70° C., Mn=704)
Divinylbenzene monomer 0.10 part The mixture above was warmed to 60° C., and then. uniformly dissolved and dispersed at 5000 rpm using the T.K. homomixer. In the resultant mixture, 10 parts of 2,2'-azobises(2,4-dimethylvaleronitrile) which is a polymerization initiator was dissolved to prepare a polymerizable monomer composition.

The polymerizable monomer composition was put in the aqueous medium, and then granulated for 15 minutes while maintaining the number of rotations of 12000 rpm. Thereafter, a stirrer was changed from the high-speed stirrer to a propeller stirring blade. Then, the polymerization was continued at a liquid temperature of 60° C. for 5 hours, the liquid temperature was increased to 80° C., and then the polymerization was continued for 8 hours. After the completion of the polymerization reaction, residual monomers were distilled off at 80° C. under reduced pressure, and then the liquid temperature was cooled to 30° C., whereby a polymer fine particle dispersion was obtained.

Next, the polymer fine particle dispersion was moved to a washing vessel, and then dilute hydrochloric acid was added under stirring to adjust the pH to 1.5, and then the mixture was stirred for 2 hours. The solid-liquid separation was performed with a filter to obtain polymer particles. Re-dispersion in water and solid-liquid separation of polymer fine particles were repeatedly performed until compounds containing phosphoric acid and calcium including calcium phosphate were sufficiently removed. Thereafter, the polymer fine particles which finally achieved solid-liquid separation were sufficiently dried with a drier to obtain toner base particles (1).

1.00 part of hydrophobic silica fine powder which was surface-treated by hexamethyldisilazane (Number average diameter of primary particles: 7 nm), 0.15 part of rutile type titanium oxide fine powder (Number average diameter of primary particles: 45 nm), and 0.50 part of rutile type titanium oxide fine powder (Number average diameter of primary particles: 200 nm) based on 100 parts of the obtained. toner base particles were dry-mixed for 5 minutes with a Henschel mixer (manufactured by NIPPON COKE &. ENGINEERING CO., LTD.) to obtain the toner (1) of the present invention.

Examples 2 to 4: Manufacturing of Toners (2) to (4)

Toners (2) to (4) of the present invention were obtained in the same manner as in Example 1, except changing the compound (1) to the compounds (15), (17), and (24), respectively, in Example 1.

Example 5: Manufacturing of Toner (5)

A toner (5) of the present invention was obtained in the same manner as in Example 1, except using 3 parts of the compound (1) and 3 parts of C.I. Pigment Red 122 (manufactured by Clariant Japan K.K., Trade name "Toner Magenta E") in place of using 6 parts of the compound (1) in Example 1.

Example 6: Manufacturing of Toner (6)

A toner (6) of the present invention was obtained in the same manner as in Example 1, except using two kinds of 3 parts of the compound (24) and 3 parts of C.I. Pigment Red 122 (manufactured by Clariant Japan K.K., Trade name "Toner Magenta E") in place of using 6 parts of the compound (1).

Comparative Examples 1 and 2: Manufacturing of Toners for Comparison (1) and (2)

Toners for comparison (1) and (2) were obtained in the same manner as in Example 1, except changing the compound (1) to the following comparative compounds (1) and (2), respectively, in Example 1.

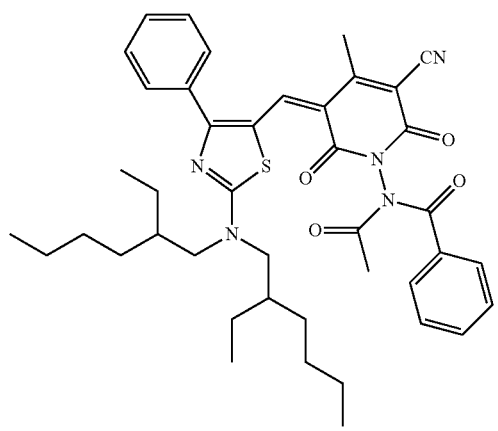

Pigment for comparison (1)

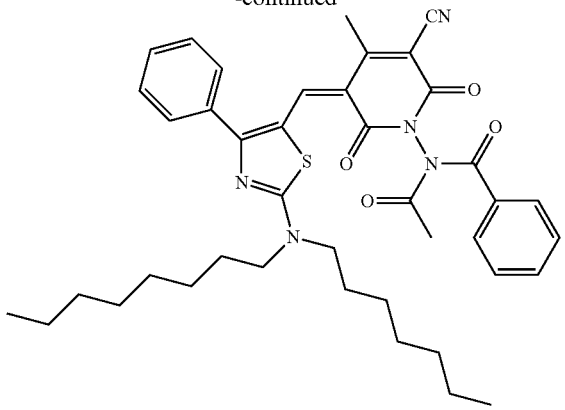

Pigment for comparison (2)

Example 7: Manufacturing of Toner (7)

82.6 parts of styrene, 9.2 parts of n-butyl acrylate, 1.3 parts of acrylic acid, 0.4 part of hexanediol acrylate, and 3.2 parts of n-lauryl mercaptan were mixed and dissolved. An aqueous solution of 1.5 parts of NEOGEN RE (manufactured by Daiichi Kogyo Seiyaku Co., Ltd.) in 150 parts of ion exchange water was added and dispersed in this solution. Further, an aqueous solution of 0.15 part of potassium peroxodisulfate in 10 parts of ion exchange water was added under slowly stirring for 10 minutes. After performing nitrogen replacement, the resultant mixture was subjected to emulsion polymerization at a temperature of 70° C. for 6 hours. After the completion. of the polymerization, the reaction liquid was cooled to room temperature, and then ion exchange water was added, whereby a resin particle dispersion liquid having a solid content concentration of 12.5% by mass and a median size on a volume basis of 0.2 μm was obtained.

100 parts of ester wax (Peak temperature of the maximum, endothermic peak in DSC measurement=70° C., Number average molecular weight Mn=704) and 15 parts of NEOGEN PK were mixed with 385 parts of ion exchange water, and then dispersed for about 1 hour using a wet jet mill JN100 (manufactured by JOKOH) to obtain a wax dispersion liquid. The concentration of the wax particle dispersion liquid was 20% by mass.

50 parts of the compound (1) which is the compound of the present invention and 15 parts of an anionic surfactant (NEOGEN PK, manufactured by Daiichi Kogyo Seiyaku Co., Ltd.) were mixed with 885 parts of ion exchange water, and then dispersed for about 1 hour using a wet jet mill JN100 (manufactured by JOKOM to obtain a dispersion liquid (1). The median diameter on a volume basis of colorant particles was 0.15 μm.

160 parts of a resin particle dispersion liquid, 10 parts of wax dispersion liquid, 10 parts of the dispersion liquid (1), and 0.2 part of magnesium sulfate were dispersed using a homogenizer (manufactured by IKA: ULTRA-TURRAX 150), and then the temperature was increased to 65° C. After stirring at 65° C. for 1 hour, it was confirmed under an optical microscope that aggregate particles having an average particle diameter of about 5.5 μm were formed. Furthermore, 2.2 parts of NEOGEN RK was added, the temperature was increased to 80° C., and then the mixture was stirred for 2 hours. The resultant mixture was cooled to room temperature, filtering was performed, the solid separated by filtration was put in 720 parts of ion exchange water, and then the mixture was dispersed and washed for 1 hour. The solid was filtered, and then dispersion and washing by ion exchange water were repeated until the electrical conductivity of the filtrate reached 150 μS/cm or less. The resultant substance was dried using a vacuum dryer to obtain toner base particles (7).

1.8 parts of silica fine powder which was subjected to hydrophobization treatment and having a specific surface area measured by the BET method of 200 m$^2$/g was mixed with 100 parts of the toner base particles (7) with a Henschel mixer (manufactured by NIPPON COKE &. ENGINEERING CO., LTD.) to obtain a toner (7).

Examples 8 to 10: Manufacturing of Toners (8) to (10)

Toners (8) to (10) of the present invention were obtained in the same manner as in Example 7, except changing the compound (1) to the compounds (15), (17), and (24), respectively, in Example 7.

Example 11: Manufacturing of Toner (11)

A toner (11) of the present invention was obtained in the same manner as in Example 7, except using 25 parts of the compound (1) and 25 parts of C.I. Pigment Red 122 (manufactured by Clariant Japan K.K., Trade name "Toner Magenta E") in place of using 50 parts of the compound (1) in Example 7.

Comparative Examples 3 and 4: Manufacturing of Toners for Comparison (3) and (4)

Toners for comparison (3) and (4) were obtained in the same manner as in Example 7, except changing the compound (1) to the comparative compounds (1) and (2), respectively, in Example 7.

Example 12: Manufacturing of Toner (12)

Polyester resin: 100 parts
(Tg of 55° C., Acid value of 20 mgKOH/g, Hydroxyl group value of 16 mgKOH/g, Peak top molecular weight Mp=4500, Number average molecular weight Mn=2300, Weight average molecular weight Mw=38000)
Compound (1) which is the compound of the present invention: 3 parts
1.4-di-t-butyl aluminum salicylate compound: 0.5 part
Paraffin wax (Maximum endothermic peak temperature of 78° C.): 5 parts The materials above were sufficiently mixed with a Henschel mixer (FM-75J type, manufactured by Mitsui Mining Co., Ltd.), and then kneaded at a Feed amount of 60 kg/hr with a biaxial kneader (PCM-45 type, manufactured by Ikegai Iron Works, Ltd.) with a temperature set to 130° C. (The temperature of the kneaded. substance when discharged was about 150° C.) The obtained kneaded substance was roughly pulverized with a hammer mill, and then finely pulverized with a mechanical pulverizer (T-250: manufactured by FREUND TURBO) at a Feed amount of 20 kg/hr. Furthermore, the obtained toner pulverized substances were classified by a multi-division classifier utilizing the Coanda effect to thereby obtain toner base particles (12).

1.8 parts of silica fine powder which was subjected to hydrophobization treatment and having a specific surface area measured by the BET method of 200 m$^2$/g was mixed with 100 parts of the toner base particles (12) with a Henschel mixer (manufactured by NIPPON COKE &. ENGINEERING CO., LTD.) to obtain a toner (12).

Examples 13 to 15: Manufacturing of Toners (13) to

Toners (13) to (15) of the present invention were obtained in the same manner as in Example 12, except changing the compound (1) to the compound (15), (17), and (24) respectively, in Example 12.

Example 16: Manufacturing of Toner (16)

A toner (16) of the present invention was obtained in the same manner as in Example 12, except using 1.5 parts of the compound (1) and 1.5 parts of 0.1. Pigment Red 122 (manufactured by Clariant Japan K.K., Trade name "Toner Magenta E") in place of using 3 parts of the compound (1) in Example 12.

Example 17: Manufacturing of Toner (17)

A toner (17) of the present invention was obtained in the same manner as in Example 12, except using 1.5 parts of the compound (24) and 1.5 parts of 0.1. Pigment Red 122 (manufactured by Clariant Japan. K.K., Trade name "Toner Magenta E") in place of using 3 parts of the compound (1) in Example 12.

Comparative Examples 5 and 6: Manufacturing of Toners for Comparison (5) and (6)

Toners for comparison (5) and (6) were obtained in the same manner as in Example 12, except changing the compound (1) to the comparative compounds (1) and (2) respectively, in Example 12.

Evaluation

The toner particles above were evaluated as follows. The evaluation results are shown in Table 1 shown below.

Particle Diameter Evaluation of Toner

The weight average particle diameter D4 and the number average particle diameter Di of the toners were measured by the following method, and then the ratio (D4/D1) was calculated and evaluated. When the D4/D1 was less than 1.35, it was judged that the particle size distribution was good.

Evaluation Criteria

A: D4/D1 is less than 1.30 (Very good particle size distribution)
B: D4/D1 is 1.30 or more and less than 1.35 (Good particle size distribution).
C: D4/D1 is 1.35 or more (Poor particle size distribution).

Method for measuring weight average particle diameter D4 and number average particle diameter D1 of toner The number average particle diameter (D1) and the weight average particle diameter (D4) of the toners were measured by the particle size distribution analysis by the Coulter method. The number average particle diameter (D1) and the weight average particle diameter (D4) of the toners were measured using a Coulter Counter TA-II or a Coulter Multisizer II (manufactured by Beckman Coulter) as a measuring apparatus according to the operation manual of the apparatus. As an electrolytic solution, an about 1% sodium chloride aqueous solution was prepared using primary sodium chloride. For example, an ISOTON-II (manufactured by Coulter Scientific Japan) can be used. As a specific measuring method, 0.1 to 5 mL of a surfactant (suitably alkyl benzenesulfonic acid salt) is added as a dispersant in 100 to 150 mL of the electrolytic aqueous solution, and further 2 to 20 mg of a measurement sample (toner) is added thereto. The electrolytic solution in which the sample is suspended is subjected to dispersion treatment for about 1 to 3 minutes with an ultrasonic dispersion machine. The obtained dispersed liquid is measured for the volume and the number of toners of 2.00 μm or more using the measuring apparatus to which a 100 μm aperture is attached, and then the volume distribution and the number distribution of the toners are calculated. Using the obtained data, the number average particle diameter (D1) determined from the number distribution of the toners, the weight average particle diameter (D4) (The median of each channel is the central value for each channel.) of the toners determined from the volume distribution of the toner particles, and D4/D1 were determined.

As the channels, 13 channels of 2.00 to 2.52 μm, 2.52 to 3.17 μm, 3.27 to 4.00 μm, 4.00 to 5.04 μm, 5.04 to 6.35 μm, 6.35 to 8.00 μm, 8.00 to 10.08 μm, 10.08 to 12.70 μm, 12.70 to 16.00 μm, 16.00 to 20.20 μm, 20.20 to 25.40 μm, 25.40 to 32.00 μm, and 32.00 to 40.30 μm are used.

As shown in Table 1, it is found that, even when the toners were manufactured by suspension polymerization, the toners having good particle size distribution were obtained.

Covering Power of Compound

The absorbance of a solution prepared by malting 20 mg of a compound in 100 mL of a solvent (toluene) was measured. The obtained absorbance was converted to the absorbance per g of the compound. The values of the "Abs." column in Table 2 show the converted absorbance.

Covering Power of Toner 0.5 g of the toners were uniformly spread on a 2 $cm^2$ glass substrate, heat press was performed under the conditions of 160° C. and 1 kg with a BIG HEATER (manufactured by Imoto Machinery Co., Ltd.), and color development property evaluation samples were produced.

The obtained color development property evaluation samples were subjected to UV spectral measurement (UV-3600, UV-VIS-NIR SPECTROPHOTOMETER, manufactured by Shimadzu Corporation) to measure the absorbance. The obtained absorbance was converted to the absorbance per g of a dye, and then the covering power was evaluated according to the following criteria. The covering power of a dye is determined by (Absorbance of chromophores)× (Number of chromophores). When the absorbance of chromophores is higher, high coloring property is achieved even when the number of chromophores is small, i.e., low concentration, so that the covering power is improved.

The evaluation was performed according to the following criteria.

TABLE 1

| | Toner No. | Colorant | Manufacturing method | D50 | D4/D1 | Particle size distribution |
|---|---|---|---|---|---|---|
| Ex. 1 | 1 | Compound (1) | Suspension polymerization method | 5.9 | 1.25 | A |
| Ex. 2 | 2 | Compound (15) | Suspension polymerization method | 5.8 | 1.13 | A |
| Ex. 3 | 3 | Compound (17) | Suspension polymerization method | 5.8 | 1.22 | A |
| Ex. 4 | 4 | Compound (24) | Suspension polymerization method | 5.2 | 1.24 | A |
| Ex. 5 | 5 | Compound (1) + P.R. 122 | Suspension polymerization method | 5.1 | 1.14 | A |
| Ex. 6 | 6 | Compound (24) + P.R. 122 | Suspension polymerization method | 6.2 | 1.21 | A |
| Ex. 7 | 7 | Compound (1) | Emulsion aggregation method | 5.9 | 1.29 | A |
| Ex. 8 | 8 | Compound (15) | Emulsion aggregation method | 6.1 | 1.27 | A |
| Ex. 9 | 9 | Compound (17) | Emulsion aggregation method | 5.7 | 1.11 | A |
| Ex. 10 | 10 | Compound (24) | Emulsion aggregation method | 5.1 | 1.21 | A |
| Ex. 11 | 11 | Compound (1) + P.R. 122 | Emulsion aggregation method | 6.0 | 1.20 | A |
| Ex. 12 | 12 | Compound (1) | Pulverization method | 6.4 | 1.31 | B |
| Ex. 13 | 13 | Compound (15) | Pulverization method | 6.2 | 1.27 | A |
| Ex. 14 | 14 | Compound (17) | Pulverization method | 6.2 | 1.32 | B |
| Ex. 15 | 15 | Compound (24) | Pulverization method | 6.3 | 1.32 | B |
| Ex. 16 | 16 | Compound (1) + P.R. 122 | Pulverization method | 6.7 | 1.31 | B |
| Ex. 17 | 17 | Compound (24) + P.R. 122 | Pulverization method | 6.3 | 1.30 | B |
| Comp. Ex. 1 | Comp. 1 | Comparative Compound (1) | Suspension polymerization method | 5.5 | 1.58 | C |
| Comp. Ex. 2 | Comp. 2 | Comparative Compound (2) | Suspension polymerization method | 5.6 | 1.20 | A |
| Comp. Ex. 3 | Comp. 3 | Comparative Compound (1) | Emulsion aggregation method | 6.3 | 1.20 | A |
| Comp. Ex. 4 | Comp. 4 | Comparative Compound (2) | Emulsion aggregation method | 6.2 | 1.17 | A |
| Comp. Ex. 5 | Comp. 5 | Comparative Compound (1) | Pulverization method | 6.8 | 1.32 | B |
| Comp. Ex. 6 | Comp. 6 | Comparative Compound (2) | Pulverization method | 6.8 | 1.32 | B |

A.: Absorbance is 110 or more (Very high covering power).
B: Absorbance is 105 or more and less than 110 (High covering power).
C: Absorbance is less than 105 (Not high covering power).

TABLE 2

|  | Toner No. | Colorant | Manufacturing method | Abs. | Evaluation |
|---|---|---|---|---|---|
| Ex. 1 | 1 | Compound (1) | Suspension polymerization method | 129.9 | A |
| Ex. 2 | 2 | Compound (15) | Suspension polymerization method | 111.4 | A |
| Ex. 3 | 3 | Compound (17) | Suspension polymerization method | 107.5 | B |
| Ex. 4 | 4 | Compound (24) | Suspension polymerization method | 154.5 | A |
| Ex. 5 | 5 | Compound (1) + P.R. 122 | Suspension polymerization method | 108.2 | B |
| Ex. 6 | 6 | Compound (24) + P.R. 122 | Suspension polymerization method | 112.7 | A |
| Ex. 7 | 7 | Compound (1) | Emulsion aggregation method | 125.3 | A |
| Ex. 8 | 8 | Compound (15) | Emulsion aggregation method | 110.4 | A |
| Ex. 9 | 9 | Compound (17) | Emulsion aggregation method | 106.1 | B |
| Ex. 10 | 10 | Compound (24) | Emulsion aggregation method | 156.6 | A |
| Ex. 11 | 11 | Compound (1) + P.R. 122 | Emulsion aggregation method | 106.2 | B |
| Ex. 12 | 12 | Compound (1) | Pulverization method | 129.4 | A |
| Ex. 13 | 13 | Compound (15) | Pulverization method | 112.8 | A |
| Ex. 14 | 14 | Compound (17) | Pulverization method | 106.5 | B |
| Ex. 15 | 15 | Compound (24) | Pulverization method | 155.7 | A |
| Ex. 16 | 16 | Compound (1) + P.R. 122 | Pulverization method | 109.1 | B |
| Ex. 17 | 17 | Compound (24) + P.R. 122 | Pulverization method | 130.4 | A |
| Comp. Ex. 1 | Comp. 1 | Comparative Compound (1) | Suspension polymerization method | 104.7 | C |
| Comp. Ex. 2 | Comp. 2 | Comparative Compound (2) | Suspension polymerization method | 104.8 | C |
| Comp. Ex. 3 | Comp. 3 | Comparative Compound (1) | Emulsion aggregation method | 103.2 | C |
| Comp. Ex. 4 | Comp. 4 | Comparative Compound (2) | Emulsion aggregation method | 103.9 | C |
| Comp. Ex. 5 | Comp. 5 | Comparative Compound (1) | Pulverization method | 104.2 | C |
| Comp. Ex. 6 | Comp. 6 | Comparative Compound (2) | Pulverization method | 104.6 | C |

*Abs. = Absorbance

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-133453, filed Jul. 2, 2015 which is hereby incorporated by reference herein in its entirety.

What is claimed is:

1. A compound having a structure represented by General Formula (1) shown below,

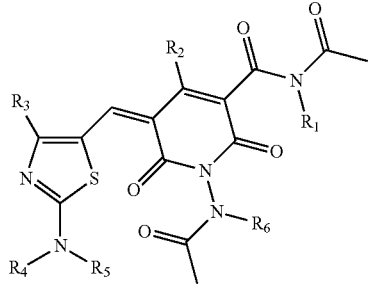

(1)

wherein, in General Formula (1), $R_1$ represents an alkyl group or an aralkyl group, $R_2$, $R_4$, and $R_5$ each independently represent an alkyl group, $R_3$ represents an alkyl group, a phenyl group not having a substituent, or a phenyl group having a substituent, the substituent in the phenyl group having the substituent is an alkyl group or an alkoxy group, and $R_6$ represents an alkyl group or an acyl group.

2. The compound according to claim 1, wherein, in General Formula (1) above, $R_3$ has a structure represented by General Formula (2) shown below,

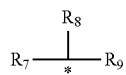

(2)

wherein, in General Formula (2), $R_7$ represents a hydrogen atom or an alkyl group, $R_8$ and $R_9$ each independently represent an alkyl group, and * represents a bonding site.

3. The compound according to claim 1, wherein, in General Formula (1) above, $R_3$ has a structure represented by General Formula (3) shown below,

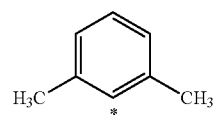

(3)

wherein, in General Formula (3), * represents a bonding site.

4. A toner comprising:
a binder resin and the compound according to claim 1.

* * * * *